United States Patent
Li et al.

(10) Patent No.: US 8,350,065 B2
(45) Date of Patent: Jan. 8, 2013

(54) 5,6-DIMETHYL XANTHONE-4-ACETIC ACID DERIVATIVES AND METHOD OF PREPARING THE SAME

(75) Inventors: Wei Li, Wuhan (CN); Guofan Xie, Wuhan (CN); Jianzhong Zhou, Wuhan (CN); Bo Yang, Wuhan (CN); Zhiqiang Qian, Wuhan (CN); Yan Chen, Wuhan (CN); Haiming Geng, Wuhan (CN); Jianming Zhou, Wuhan (CN); Lu Huang, Wuhan (CN)

(73) Assignee: Grand Pharma (China) Co., Ltd., Wuhan (CN)

( * ) Notice: Subject to any disclaimer, the term of this patent is extended or adjusted under 35 U.S.C. 154(b) by 635 days.

(21) Appl. No.: 12/581,184

(22) Filed: Oct. 19, 2009

(65) Prior Publication Data

US 2010/0099754 A1 Apr. 22, 2010

Related U.S. Application Data

(63) Continuation of application No. PCT/CN2008/071161, filed on Jun. 2, 2008.

(30) Foreign Application Priority Data

Jun. 2, 2008 (WO) ............... 2008/071161

(51) Int. Cl.
*C07D 311/80* (2006.01)
*C07D 311/82* (2006.01)
*C07D 311/86* (2006.01)
(52) U.S. Cl. ........................ 549/390; 549/392
(58) Field of Classification Search .......... None
See application file for complete search history.

(56) References Cited

PUBLICATIONS

Rewcastle et. al, Journal of Medicinal Chemistry, 1991, American Chemical Society, vol. 34, pp. 217-222.*
Cesar Portela, Carlos M. M. Afonso, Madalena M. M. Pinto, Dinora Lopes, Fatima Nogueira and Virgilio do Rosario, Synthesis and Antimalarial Properties of New Chloro-9H-xanthones with an Aminoalkyl Side Chain, Chemistry & Biodiversity, vol. 4, pp. 1508-1519, Jul. 16, 2007.*

* cited by examiner

*Primary Examiner* — Andrew D Kosar
*Assistant Examiner* — Laura Daniel
(74) *Attorney, Agent, or Firm* — Matthias Scholl P.C.; Matthias Scholl

(57) ABSTRACT

A method of preparation of 5,6-dimethylxanthone-4-acetic acid (DMXAA) and derivatives thereof. The derivatives are represented by formula (I), wherein R represents totally 1 to 2 substitutes at 1, 2, 3, 7, and 8 position selected from a lower alkyl, halogen, $CF_3$, CN, $NO_2$, $NH_2$, $CH_2COOH$, $OR_2$, OH, $NHSO_2R_2$, $SR_2$, $CH_2CONHR_2$ or $NHR_2$, and $R_2$ represents a lower alkyl, or a lower alkyl having OH, $NH_2$, or $OCH_3$. The invention further provides a pharmaceutical composition having such derivatives used as excellent antitumor and antibacterial agents.

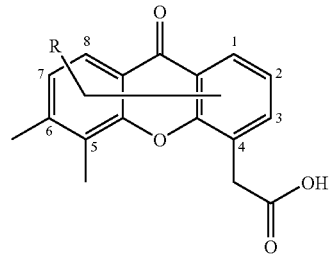

I

8 Claims, No Drawings

5,6-DIMETHYL XANTHONE-4-ACETIC ACID DERIVATIVES AND METHOD OF PREPARING THE SAME

CROSS-REFERENCE TO RELATED APPLICATIONS

This application is a continuation of International Patent Application No. PCT/CN2008/071161 with an international filing date of Jun. 2, 2008, designating the United States, now pending, and further claims priority benefits to Chinese Patent Application No. 200710053403.2 filed Sep. 28, 2007. The contents of all of the aforementioned applications, including any intervening amendments thereto, are incorporated herein by reference.

BACKGROUND OF THE INVENTION

1. Field of the Invention

The invention relates to a compound and a method of preparing the same, and more particularly to 5,6-dimethyl xanthone-4-acetic acid (DMXAA) derivatives and its preparation method, as well as its use as anticancer and antibacterial drugs.

2. Description of the Related Art

DMXAA is a tumor angiogenesis inhibitor and used for the treatment of cancers. Nowadays, it has been applying in the clinical trial phase III. Rewcastle et al. disclosed a method of preparation of DMXAA, as shown in Scheme 1 (Rewcastle et al.; J. Med. Chem. 1991, 34, 217).

Scheme 1:

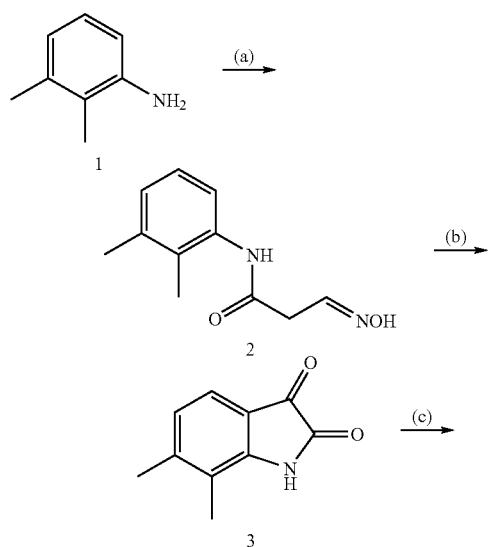

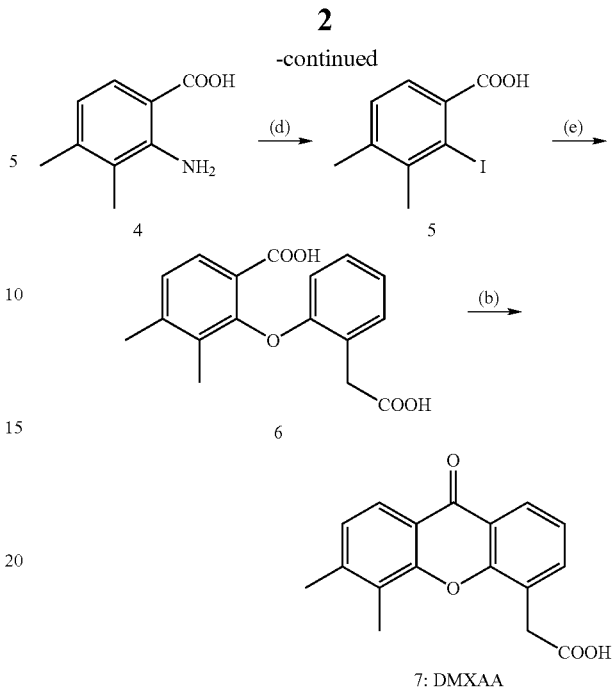

(a) Cl₃CCH(OH)₂/NH₂OH
(b) H₂SO₄
(c) H₂O₂/KOH
(d) HNO₂/KI
(d) 2-Hydroxyphenylacetic acid/Cu/TDA-1

The starting material of 2,3-dimethyl aniline (1) was mixed and condensed with hydroxylamine and chloral hydrate to yield isonitrosoacetanilide (2), then to yield isatin (3) by acid-catalyzed cyclization and 2-amino-3,4-dimethyl-benzoic acid (4) by an oxidative ring cleavage reaction. The total yield of the first three steps was 37%. The steps involved in hydroxylamine and chloral hydrate, both of which were toxic. Additionally, the steps were a multi-phase reaction, requiring careful control on the reaction time and temperature. Under carefully-controlled conditions, 2-amino-3,4-dimethyl-benzoic acid (4) was diazotized to yield an iodide (5). The iodide was condensed with 2-hydroxyphenylacetic acid to yield 2-[2-(carboxymethyl)phenoxy]-3,4-dimethyl-benzoic acid (6), which was further cyclized to yield DMXAA. The total yield of the six steps was about 12%.

Atwell et al. disclosed another method of preparation of the key intermediate of 2-amino-3,4-dimethyl-benzoic acid (4) (Atwell et al.; Eur. J. Med. Chem., 2002, 37, 825), as shown in Scheme 2.

Scheme 2:

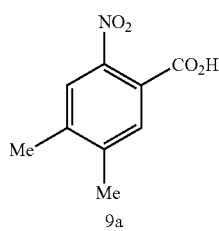

+

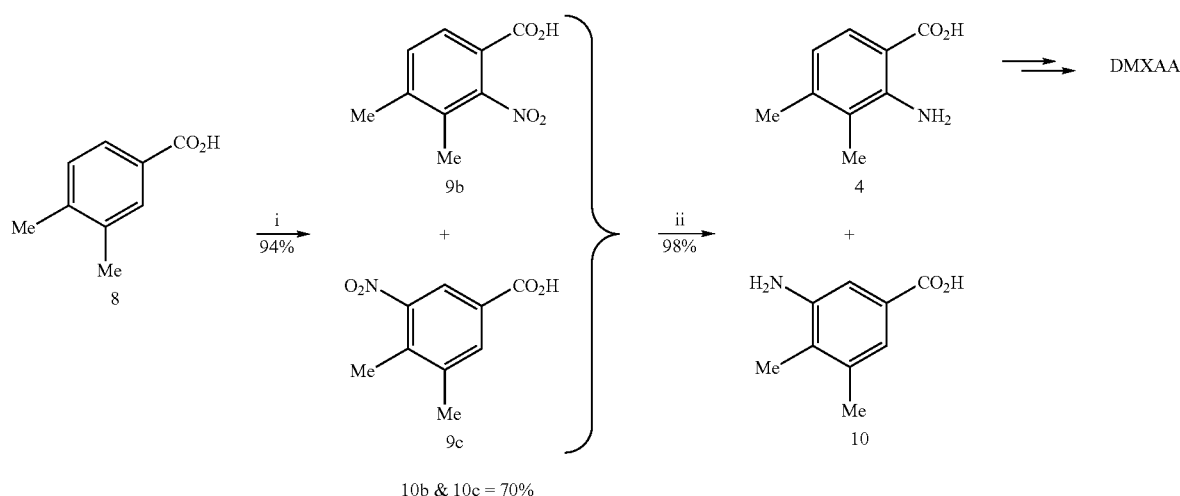

(i) tHNO₃;
(ii) H₂/Pd/C.

3,4-dimethyl-benzoic acid was directly nitrified and condensed to yield a mixture consisting of nitro isomers 9a, 9b, and 9c. The ratio of 9a to 9b to 9c was 1:8:2. The mixture was recrystallized from acetic acid to remove 9a, and the ratio of the remaining 9b to 9c was 3.4:1. After catalytic hydrogenation, the remaining mixture was transformed into a sodium salt solution, which was further neutralized with acetic acid to give a pure crystal of 2-amino-3,4-dimethyl-benzoic acid (4) (the purity was 96%; the total yield was 42%). An improved method of preparation of DMXAA was also disclosed in the above-mentioned literature. Compared with Scheme 1 (32%), Scheme 2 had a higher yield of 2-amino-3,4-dimethyl-benzoic acid (4). However, step-by-step recrystallization limited the industrial production of DMXAA.

Rewcastle et al. taught a method of improving the first step of preparation of DMXAA, i.e., from the starting material of 2,3-dimethyl aniline (1) to isonitrosoacetanilide (2) (Rewcastle et al., Tet. Lett., 2005, 46, 8719), as shown in Scheme 3.

Scheme 3:

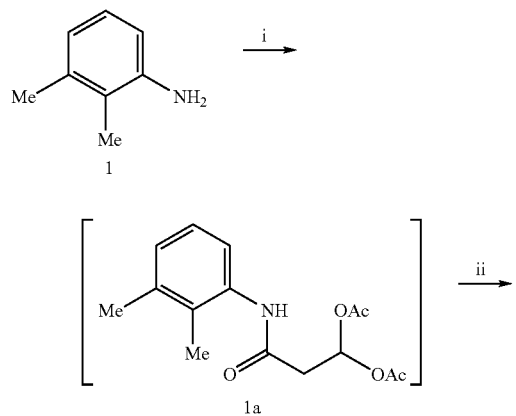

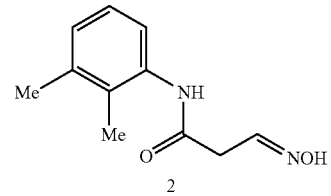

2,3-dimethyl aniline was acylated with 2,2-diacetoxy-acetyl chloride to give a crude product of diacetate (1a). The crude product was contacted with hydroxylamine to give isonitrosoacetanilide (2).

Compared with Scheme 1 (Rewcastle et al.; J. Med. Chem. 1991, 34, 217) where the reaction was non-homogeneous and the yield was 54%, the reaction in Scheme 3 was homogeneous and the yield was 83%.

However, all the above-mentioned methods have disadvantages such as complicated process, low yield, serious pollution, and difficulty for industrial production.

SUMMARY OF THE INVENTION

In view of the above-described problems, it is one objective of the invention to provide a method of preparing 5,6-dimethylxanthenone-4-acetic acid and derivatives thereof that has high yield and causes no pollution.

It is another objective of the invention to provide a compound of 5,6-dimethylxanthenone-4-acetic acid derivatives that is more effective for treatment of cancers.

It is still another objective of the invention to provide a pharmaceutical composition at least comprising 5,6-dimethylxanthenone-4-acetic acid or derivatives thereof that is more effective for treatment of cancers.

To achieve the above objectives, in accordance with one embodiment of the invention, there is provided a method of preparing 5,6-dimethylxanthenone-4-acetic acid and derivatives thereof, comprising the steps of (as shown in Scheme 4):

Scheme 4

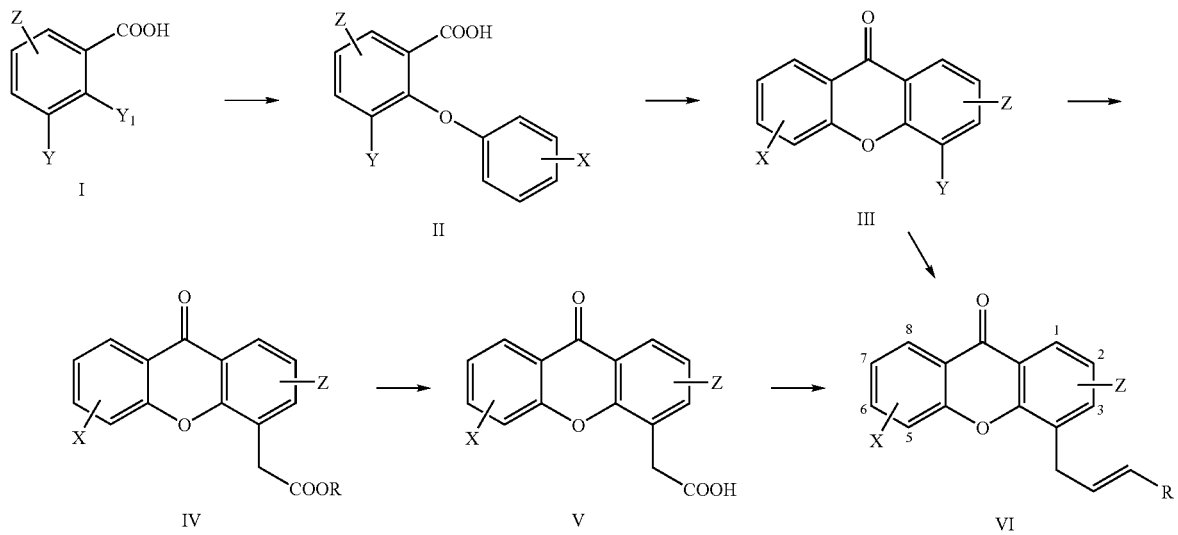

wherein X represents H, or totally 0 to 4 substitutes at 5-8 position selected from R, OR, halogen, $NO_2$, $NR_2$, SR, $SO_2R$, $CF_3$, CN, $CO_2R$, CONHR, or COR, wherein R represents a $C_{1-6}$ aliphatic group, $C_{3-6}$ saturated ring substitute, OH, methoxy, $NH_2$, or $N(methyl)_2$, and $R_2$ represents a lower alkyl, or a lower alkyl comprising OH, $NH_2$, or $OCH_3$;

Y represents a halogen selected from Cl, Br, or I;

$Y_1$ represents a halogen selected from Cl, Br, or I; and

Z represents H, or totally 0 to 3 substitutes at 1-3 position selected from R, OR, halogen, $NO_2$, $NR_2$, SR, $SO_2R$, $CF_3$, CN, $CO_2R$, CONHR, or COR, wherein R represents a $C_{1-6}$ aliphatic group, $C_{3-6}$ saturated ring substitute, OH, methoxy, $NH_2$, or $N(methyl)_2$, and $R_2$ represents a lower alkyl, or a lower alkyl comprising OH, $NH_2$, or $OCH_3$.

In a class of this embodiment, X represents 5,6-dimethyl, 5,6-dimethoxy, 5-Cl, 6-methyl, 5-Cl, or 6-methoxy; Y represents Br; $Y_1$ represents I; and Z represents H, 2-methyl, 2-methoxy, or 2-Cl.

Particularly, X represents 5,6-dimethyl; Y represents Br; $Y_1$ represents I; and Z represents H.

The first step is a condensation reaction between a substituted carboxylic acid and a substituted phenol. The second step is a dehydration-cyclization reaction. The third step is an esterification reaction. The fourth step is a hydrolysis reaction. The fifth step is a substitution reaction.

In a class of this embodiment, during the conversion reaction of the compound (I) into the compound (II), 2,3-dimethylphenol or 2,3,5-trimethylphenol is used.

In a class of this embodiment, during the conversion reaction of the compound (I) into the compound (II), 3-bromo-2-iodo benzoic acid, 3-bromo-2-iodo-5-methyl-benzoic acid, or 2-iodo-3,4,5-trimethyl benzoic acid is used.

In a class of this embodiment, during the conversion reaction of the compound (I) into the compound (II), a molar ratio of the substituted carboxylic acid to the substituted phenol is 1:1.8, particularly 1:1.07.

In a class of this embodiment, during the conversion reaction of the compound (I) into the compound (II), CuCl and tris(2-(2-methoxyethoxy)ethyl)amine is used as catalysts.

In a class of this embodiment, during the conversion reaction of the compound (II) into the compound (III), sulfuric acid, methanesulfonic acid, polyphosphoric acid, or polyphosphate is used as a dehydration-cyclization agent.

In a class of this embodiment, during the conversion reaction of the compound (III) into the compound (IV), a palladium-containing agent and complex are used as catalysts, and the complex is 1,3-bi-(2,6-diisopropylphenyl)imidazole chloride.

Based on the method of preparing 5,6-dimethylxanthenone-4-acetic acid and derivatives thereof, there is provided a compound of formula (I)

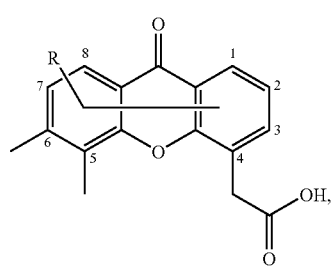

I wherein R represents totally 1 to 2 substitutes at 1, 2, 3, 7, and 8 position selected from a lower alkyl, halogen, $CF_3$, CN, $NO_2$, $NH_2$, $CH_2COOH$, $OR_2$, OH, $NHSO_2R_2$, $SR_2$, $CH_2CONHR_2$ or $NHR_2$, and $R_2$ represents a lower alkyl, or a lower alkyl comprising OH, $NH_2$, or $OCH_3$. Any two R at adjacent positions together represent a group of —CH═CH—CH═CH—, so that an additional benzo ring or a salt thereof is formed.

In a class of this embodiment, the compound is compound is 2,5,6-trimethylxanthenone-4-acetic acid or a sodium salt thereof, having formula of

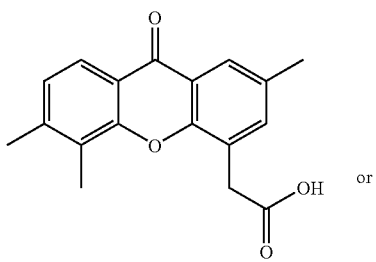 or

-continued

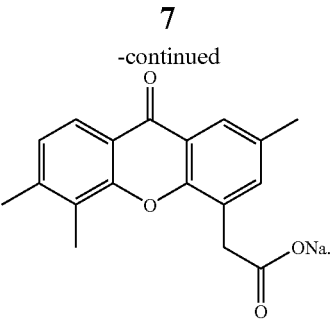

In a class of this embodiment, the compound is 5,6,7-trimethylxanthenone-4-acetic acid or a sodium salt thereof, having formula of

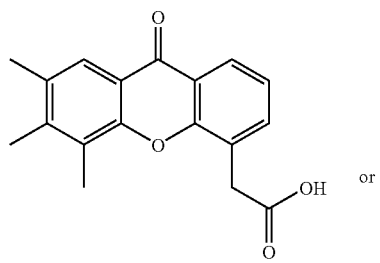

or

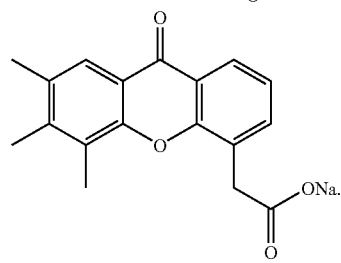

In a class of this embodiment, the compound is 5,6,8-trimethylxanthenone-4-acetic acid or a sodium salt thereof, having formula of

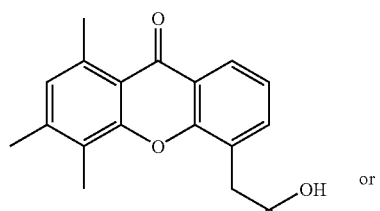

or

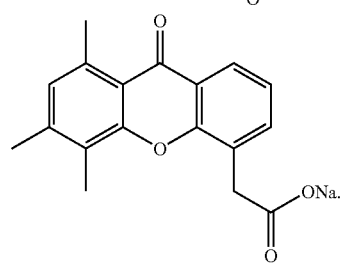

In another aspect, provided is a compound represented by formula of

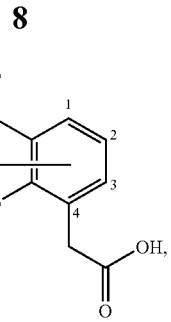

wherein R' represents totally 1 to 2 substitutes at 1-8 position selected from a lower alkyl, halogen, $CF_3$, CN, $NO_2$, $NH_2$, $CH_2COOH$, OR, OH, $NHSO_2R$, SR, $CH_2CONHR$, NHR, $OCH_3$, or a benzene ring where one or two —CH= is substituted with —N=, wherein R represents an alkyl. Any two R' at adjacent positions together represent a group of —CH=CH—CH=CH—, so that an additional benzo ring or a salt thereof is formed.

In accordance with another embodiment of the invention, further provided a pharmaceutical composition having excellent anticancer and antibacterial activity, comprising a compound of formula (I)

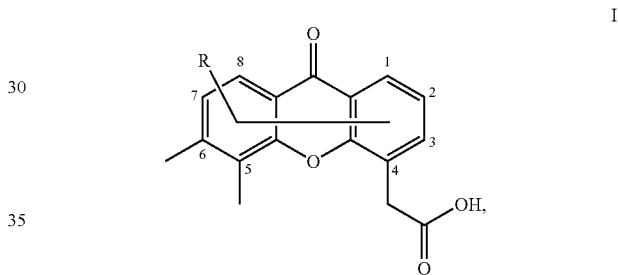

and/or a pharmaceutically acceptable salt thereof.

In a class of this embodiment, the pharmaceutical composition further comprises a carrier or a diluter.

In a class of this embodiment, the compound of formula (I) and a pharmaceutically acceptable salt thereof is mixed with an excipient to form an absorbable dosage form including but not limited to buccal tablets, tablet, capsules, tinctures, suspension, syrup, or film.

In Scheme 4 for preparing 5,6-dimethylxanthenone-4-acetic acid and derivatives thereof, the intermediate III can also be prepared by the method of Scheme 1 (Rewcastle et al.; J. Med. Chem. 1991, 34, 217).

In one embodiment of the invention, a substituted benzoic acid having two halogen atoms is condensed with a substituted phenol to yield a substituted 2-phenoxybenzoic acid (II), which is dehydrated to yield xanthone. The total yield is about 80%. The halogen atom can be substituted with an acetoxy. Here optionally provided are two methods. The one is that aryl halide is contacted with diethyl malonate (Ozdemir et al., Tetradedron Letters, 2004, 45, 5823-5825):

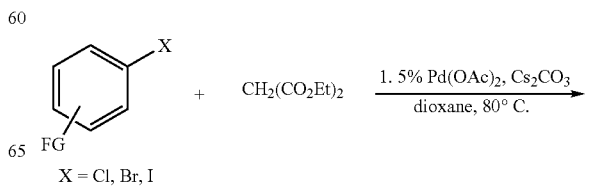

-continued

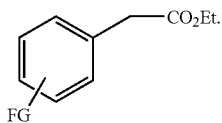

The other is that aryl halide is contacted with allylic acetate to yield a framework of aryl allyl:

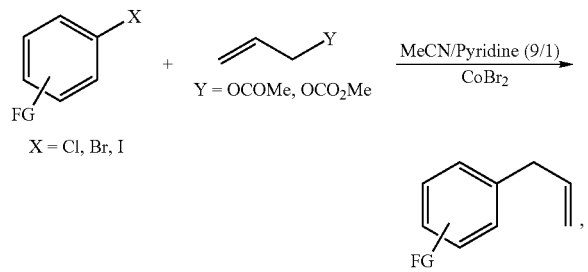

wherein FG represents an active group.

Allylic carbonate or allylic halide has been disclosed (Gomes et al., J. Org. Chem., 2003, 68, 1142-1145).

The resultant xanthone-4-acetate or 4-allyl xanthone is hydrolyzed or oxided to yield xanthone-4-acetic acid.

The preparation of the above compounds from respective starting materials is described in the Examples hereinafter.

Studies show these novel xanthone-4-acetic acid derivatives represented by formula (I) have stronger anticancer and antibacterial activity than DMXAA, so they can be processed into excellent anticancer and antibacterial drugs.

Xanthone-4-acetic acid and salts thereof represented by formula (I) can also be prepared by the method.

For example, a substituted 2-phenoxybenzoic acid represented by formula of

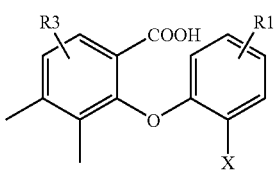

is dehydrated and cyclized to yield xanthone represented by formula of

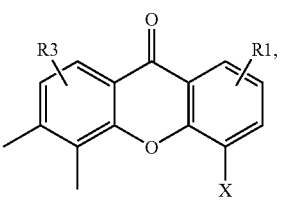

wherein $R_1$ represents H or has the same definition as R for formula (I), $R_3$ is defined as $R_1$, there is at most one H represented by $R_1$ and $R_3$, and X represents a halogen.

Diethyl malonate is arylated under catalysis of palladium and the resultant compound is decarboxylated to yield xanthone-4-ethyl acetate represented by formula of

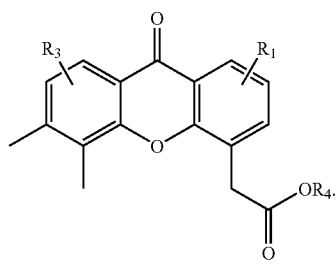

The compound is hydrolyzed with sodium hydroxide to yield xanthone-4-acetic acid of formula (I). If necessary, the resultant compound can be transformed into a base or salt thereof.

Xanthone-4-acetic acid and salts thereof represented by formula (I) can also be prepared by oxidation of allylic xanthone represented by formula of

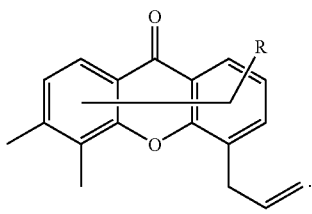

If necessary, xanthone-4-acetic acid of formula (I) can be transformed into a salt thereof.

TABLE 1

Melting point and molecular weight of part of 5,6-dimethyl xanthone-4-acetic acid derivatives

| No. | $R_1$ | Melting Point (° C.) | Molecular weight |
|---|---|---|---|
| 1 | H | 259-260 | 282.30 |
| 2 | 7-$CH_3$ | 265-267 | 296.33 |
| 3 | 8-$CH_3$ | 261-263 | 296.33 |
| 4 | 2-$CH_3$ | 271-273 | 296.33 |

Advantages of the invention are summarized below:

1) The starting materials are a substituted benzoic acid and a substituted phenol, so the synthesis route is much shorter, has higher yield, and no toxic reagent is used; and 2) The preparation method involves no low temperature or exothermic reaction, and most of reactions only need water as a medium, so the method is easier to control and suitable for industrial production.

DETAILED DESCRIPTION OF THE EMBODIMENTS

For further illustrating the invention, experiments detailing the preparation of 5,6-dimethylxanthenone-4-acetic acid and derivatives thereof are described below. It should be noted that the following examples are intended to describe and not to limit the invention.

EXAMPLE 1

Preparation of 5,6-dimethyl xanthone-4-acetic acid (DMXAA) from 3-bromo-2-iodo-benzoic acid

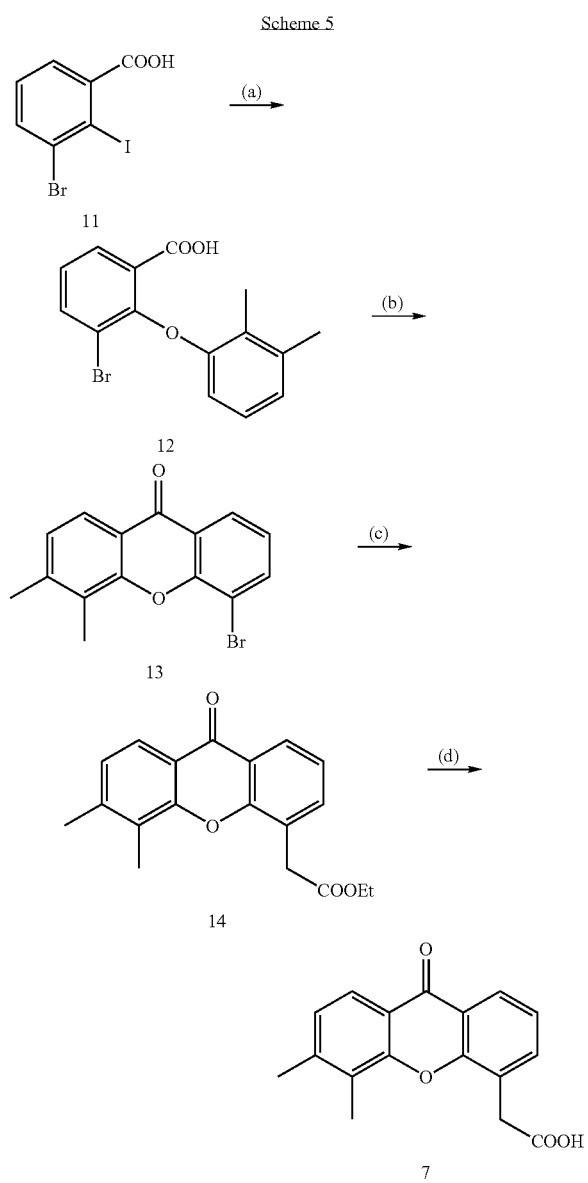

Scheme 5

(a) 2,3-dimethylphenol/Cu/TDA-1 (b) H₂SO₄ (c) CH₂(COOEt)₂/Pd (d) NaOH

As shown in the Scheme, at the presence of 10% by mole of CuCl and 10% by mole of tris(2-(2-methoxyethoxy)ethyl) amine (TDA-1), 3-bromo-2-iodo benzoic acid was contacted with 2,3-dimethylphenol to yield phenoxybenzoic acid. Without purification, the phenoxybenzoic acid was directly dehydrated and cyclized by reagents such as sulfuric acid, methanesulfonic acid, polyphosphoric acid, or polyphosphate to yield dimethylxanthone. Diethyl malonate was arylated by the dimethylxanthone under catalysis of palladium to yield 5,6-dimethylxanthone-4-ethyl acetate which was hydrolyzed to yield DMXAA.

Preparation of 3-bromo-2-(2,3-dimethylphenol)benzoic acid (12)

3-bromo-2-iodo benzoic acid (11) (2.56 g, 7.83 mmol) was dissolved in a KOH solution (KOH 536 mg, 9.6 mmol; H₂O 5 mL). The mixture was condensed under vacuum at 100° C. and the resultant solid was heated under vacuum at 100° C. for 12 h to yield a dried potassium salt. Metallic sodium (200 mg, 8.35 mmol) was dissolved in 100 mL of MeOH, and 2,3-dimethylphenol (1.09 g, 8.35 mmol) was added. The mixture was condensed and heated under vacuum at 100° C. for 12 h to yield a dried sodium salt. The sodium salt was dissolved in 15 mL of anhydrous dimethyl sulphoxide, and then tris(2-(2-methoxyethoxy)ethyl)amine (TDA-1, 1.0 mL) was added. The mixture was stirred to reach homogeneity at room temperature under anhydrous conditions, and then CuCl (350 mg) and potassium salt powders of the compound 11 were added. The resultant mixture was stirred at 85° C. for 4 h, cooled down to room temperature, washed with a NaOH solution (NaOH 200 mg, water 100 mL), filtered with diatomite, and acidified with 1 N HCl to pH value at 2-3. A semisolid precipitate was collected, washed with water, and dried to yield a crude product of 3-bromo-2-(2,3-dimethylphenol)-benzoic acid (12) (2.36 g, 7.35 mmol, 75%). The crude product can be used for next reaction directly without purification.

Preparation of 4-bromo-5,6-dimethylxanthone (13)

The crude product of 3-bromo-2-(2,3-dimethylphenol)-benzoic acid (12) (2.36 g, 7.35 mmol) was added to a stirring sulfuric acid solution (concentrated sulfuric acid 55 mL, water 20 mL). The mixture was allowed to react for 30 min at 90° C., and then cooled down to room temperature, diluted with 200 mL of ice water, and filtered. The resultant solid was washed with water, dried, and recrystallized from EtOAc/MeOH to yield a light yellow solid, i.e. 4-bromo-5,6-dimethylxanthone (13) (2.0 g, 90%): Mp(EtOAc/MeOH) 230-231° C.; $^1$H-NMR [(CD$_3$)$_2$SO] δ 8.10 (dd, J=7.9, 1.6 Hz, H1), 7.91 (d, J=8.2 Hz, H8), 7.77 (dd, J=7.2, 1.5, H3), 7.43 (dd, J=7.6, 7.6 Hz, H2), 7.26 (d, J=8.0 Hz, H7), 2.41 (s, 3H, —CH$_3$), 2.38 (s, 3H, —CH$_3$); $^{13}$C-NMR δ 171.6, 153.6, 152.1, 143.3, 136.9, 128.0, 125.6, 125.3, 124.5, 123.9, 120.2, 120.0, 119.7, 20.3, 12.4.

Preparation of 5,6-dimethylxanthone-4-ethyl acetate (14)

Powdery 4-bromo-5,6-dimethylxanthone (13) (2.2 g, 7.25 mmol), 1,3-bi-(2,6-diisopropylphenyl)imidazole chloride (Ipr. HCl, 60 mg, 0.15 mmol, 2% by mole), Pd(OAc)₂ (35 mg, 2% by mole), Cs₂CO₃ (4.7 g, 14.5 mmol), diethyl malonate (1.16 g, 7.25 mmol), and 20 mL of dioxane were mixed. The mixture was allowed to react at 80° C. for 24 h, and then cooled down to room temperature, diluted with 100 mL of EtOAc, and filtered to yield a black precipitate. The filtrate was condensed and recrystallized from EtOAc/MeOH to yield a light yellow solid, i.e. 5,6-dimethylxanthone-4-ethyl acetate (14) (2.0 g, 90%): Mp(EtOAc/MeOH) 209-211° C.; $^1$H-NMR[(CD$_3$)$_2$SO] δ 8.09 (dd, J=7.9, 1.6 Hz, H1), 7.90 (d, J=8.1 Hz, H8), 7.78 (dd, J=7.2, 1.5, H3), 7.40 (dd, J=7.6, 7.6 Hz, H2), 7.27 (d, J=8.1 Hz, H7), 4.15 (m, 2H), 3.97 (s, 2H, —CH$_2$), 2.40 (s, 3H, —CH$_3$), 2.35 (s, 3H, —CH$_3$), 2.14 (m, 3H). $^{13}$C-NMR δ 175.0, 171.6, 153.6, 152.1, 143.3, 136.9, 128.0, 125.6, 125.3, 124.5, 123.9, 120.2, 120.0, 119.7, 60.2, 53.3, 20.3, 12.4.

Preparation of 5,6-dimethylxanthone-4-sodium acetate

During the process of preparation, 5,6-dimethylxanthone-4-acetic acid required conserving in dark. 5,6-dimethylxanthone-4-ethyl acetate (96 g, 0.311 mol), 350 mL of methanol, and a NaOH solution (NaOH 24.88 g, 0.622 mol; $H_2O$ 350 mL) were mixed. The mixture was heated to make 5,6-dimethylxanthone-4-ethyl acetate dissolved completely, stirred at 40° C., hydrolyzed completely, acidified with acetic acid to yield a white precipitate, filtered, and dried to yield a crude product. To the crude product, 350 mL of methanol and a $NaHCO_3$ solution ($NaHCO_3$ 31.34 g, 0.373 mol; $H_2O$ 350 ml) were added. The mixture was heated to make 5,6-dimethylxanthone-4-acetic acid dissolved completely, evaporated, and condensed to yield a crude product of 5,6-dimethylxanthone-4-sodium acetate. The crude product was dried overnight at 100° C. in an oven, and then added to 1600 mL of methanol, refluxed by heating for an hour, and filtered with a diatomite. The diatomite was washed with 500 mL of hot methanol, and the filtrate was combined and condensed under vacuum until crystal occurred. The filtrate was cooled to room temperature, frozen overnight, and filtered to yield a crystal of 5,6-dimethylxanthone-4-sodium acetate. The crystal was washed with 300 mL of ice methanol and 500 mL of hexane separately, and dried at 100° C. for 48 h to yield 62 g of pure 5,6-dimethylxanthone-4-sodium acetate (66%), which was measured by $^1$H-NMR, HPLC purity 100%. The mother solution was condensed and recrystallized from methanol to yield 22 g of 5,6-dimethylxanthone-4-sodium acetate (23%), HPLC purity >98%.

The similar reaction was substituted with 3-bromo-2-iodo benzoic acid (as shown in Scheme 6 hereinafter) or trimethyltryptophan to yield a substituted 2-phenoxybenzoic acid.

Following the method in Example 1, the crude 2-phenoxybenzoic acid was cyclized by sulfuric acid to yield a substituted 4-bromo-xanthone, and the total yield was 90%.

At the presence of palladium and ligands, the substituted 4-bromo-xanthone was contacted with diethyl malonate to yield substituted xanthone-4-ethyl acetate which was hydrolyzed to yield DMXAA.

EXAMPLE 2

Preparation of 2,5,6-trimethyl xanthone-4-acetic acid from 3-bromo-2-iodo-benzoic acid

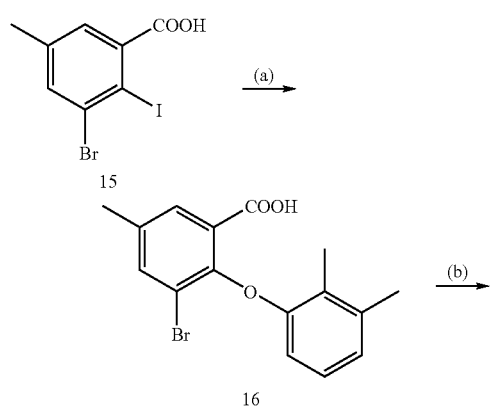

Scheme 6

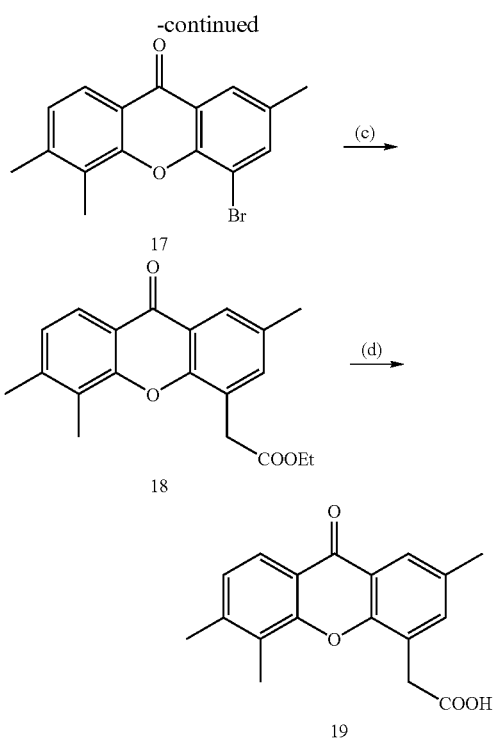

(a) 2,3-dimethylphenol/Cu/TDA-1
(b) $H_2SO_4$
(c) $CH_2(COOEt)_2$/Pd
(d) NaOH

Preparation of 3-bromo-2-(2,3-dimethylphenoxy)-5-methyl-benzoic acid (16)

Following the method in Example 1, a crude product of compound 16 was prepared from a starting material of 3-bromo-2-iodo-5-methyl benzoic acid, and the yield was 76%.

Preparation of 4-bromo-2,5,6-trimethylxanthone (17)

Following the method in Example 1, the crude 3-bromo-2-(2,3-dimethylphenoxy)-5-methyl-benzoic acid (16) was treated with sulfuric acid and recrystallized from EtOAc/MeOH to yield a light yellow solid, and the yield was 91%: Mp (EtOAc/MeOH) 236-238° C.; $^1$H-NMR [$(CD_3)_2SO$] δ 8.12 (s, 1H), 8.10 (d, J=7.9 Hz, 1H), 7.75 (d, J=7.9 Hz, 1H), 7.42 (s, 1H), 2.55 (s, 3H), 2.46 (s, 3H); $^{13}$C-NMR δ 171.6, 153.6, 152.1, 143.3, 136.9, 128.0, 125.6, 125.3, 124.5, 123.9, 120.2, 120.0, 119.7, 21.8, 20.3, 12.4.

Preparation of 2,5,6-trimethylxanthone-4-ethyl acetate (18)

Refined 4-bromo-2,5,6-trimethylxanthone (17) (2.3 g, 7.25 mmol), 1,3-bi-(2,6-diisopropylphenyl) imidazole chloride (Ipr. HCl, 60 mg, 0.15 mmol, 2% by mole), $Pd(OAc)_2$ (35 mg, 2% by mole), $Cs_2CO_3$ (4.7 g, 14.5 mmol), diethyl malonate (1.16 g, 7.25 mmol), and 20 mL of dioxane were mixed. The mixture was heated at 80° C. for 24 h, then cooled down to room temperature, diluted with 100 mL of ethyl acetate, and filtered to yield a black precipitate. The filtrate was condensed and recrystallized from EtOAc/MeOH to yield a light yellow solid (18) (2.1 g, 92%): Mp(EtOAc/MeOH) 209-211°

C.; $^1$H-NMR [(CD$_3$)$_2$SO] δ 8.16 (s, 1H), 8.13 (d, J=7.9 Hz, 1H), 7.74 (d, J=7.9 Hz, 1H), 7.43 (s, 1H), 3.48 (m, 2H), 2.55 (s, 3H), 2.46 (s, 3H), 2.22 (m, 3H); $^{13}$C-NMR δ 175.0, 171.6, 153.6, 152.1, 143.3, 136.9, 128.0, 125.6, 125.3, 124.5, 123.9, 120.2, 120.0, 119.7, 60.1, 53.3, 22.3, 20.3, 12.4.

Preparation of 2,5,6-trimethylxanthone-4-sodium acetate

Following the method in Example 1, the title compound was prepared.

EXAMPLE 3

Preparation of 5,6,7-trimethylxanthone-4-acetic acid from 2-iodo-3,4,5-trimethyl benzoic acid

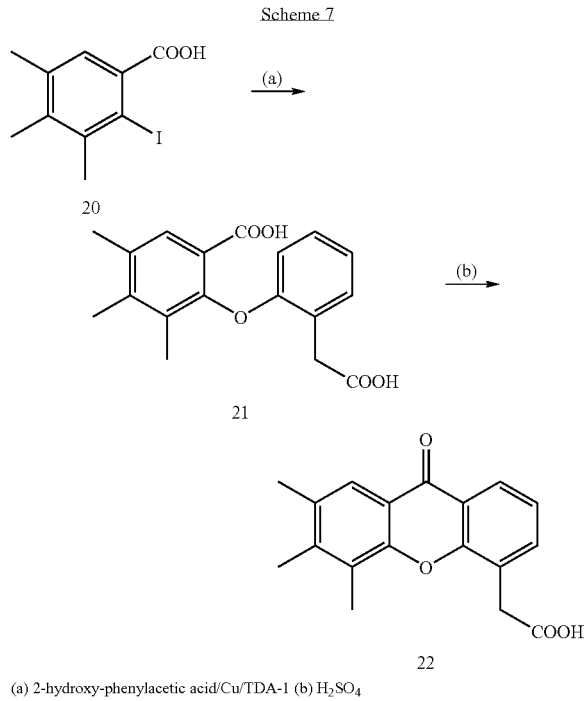

(a) 2-hydroxy-phenylacetic acid/Cu/TDA-1 (b) H$_2$SO$_4$

As shown in Scheme 7, 2-iodo-3,4,5-trimethyl benzoic acid (prepared by the method disclosed by Suzuki et al, Bull. Chem. Soc. Jpn., 1971, 44, 2871) was contacted with 2-hydroxyphenylacetic acid to yield 2-[2-(carboxymethyl)phenoxy]-3,4,5-trimethyl benzoic acid which was dehydrated and cyclized to yield 7-MeDMXAA, and the total yield was 68%.

Preparation of 2-[2-(carboxymethyl)phenoxy]-3,4,5-trimethyl benzoic acid (21)

2-iodo-3,4,5-trimethyl benzoic acid (2.41 g, 8.3 mmol) was dissolved in a KOH solution (KOH 536 mg, 9.6 mmol; H$_2$O 5 mL). The mixture was condensed under vacuum at 100° C. and the resultant solid was heated under vacuum at 100° C. for 12 h to yield a dried potassium salt. Metallic sodium (284 mg, 12.3 mmol) was dissolved in 100 mL of MeOH, and 2-hydroxyphenylacetic acid (1.27 g, 8.35 mmol) was added. The mixture was condensed and dried under vacuum at 100° C. for 12 h to yield an anhydrous disodium salt. The disodium salt was dissolved in 15 mL of anhydrous dimethyl sulphoxide, and then tris(2-(2-methoxyethoxy)ethyl)amine (TDA-1, 1.0 mL) was added. The mixture was stirred to reach homogeneity at room temperature under anhydrous conditions, and then CuCl (350 mg) and 2-iodo-3 4,5-trimethyl potassium benzoate powders were added. The resultant mixture was stirred at 85° C. for 4 h, cooled down to room temperature, washed with a NaOH solution (NaOH 200 mg, water 100 mL), filtered with diatomite, and acidified with 1 N HCl to pH value at 2-3. A solid precipitate was collected, washed with water, and dried to yield a crude product (2.3 g, 73%). The crude product can be used for next reaction directly without purification.

Preparation of 5,6,7-trimethyl xanthone-4-acetic acid (22)

The crude product powder (21) (2.36 g, 6.23 mmol) was added to a stirring sulfuric acid solution (concentrated sulfuric acid 55 mL, water 20 mL). The mixture was allowed to react for 30 min at 90° C., and then cooled down to room temperature, diluted with 200 mL of ice water, and filtered. The resultant solid was washed with water, dried, and recrystallized from EtOAc/MeOH to yield a light yellow solid (1.9 g, 88%): Mp (EtOAc/MeOH) 265-267° C.; $^1$H-NMR [(CD$_3$)$_2$SO] δ 12.63 (brs, 1H, —COOH), 8.09 (dd, J=7.9, 1.6 Hz, H1), 7.90 (s, H8), 7.78 (dd, J=7.2, 1.5, H3), 7.40 (dd, J=7.6, 7.6 Hz, H2), 3.97 (s, 2H, —CH$_2$), 2.43 (s, 3H, —CH$_3$), 2.40 (s, 3H, —CH$_3$), 2.33 (s, 3H, —CH$_3$).

EXAMPLE 4

Preparation of 5,6,8-trimethylxanthone-4-acetic acid from 3-bromo-2-iodo benzoic acid

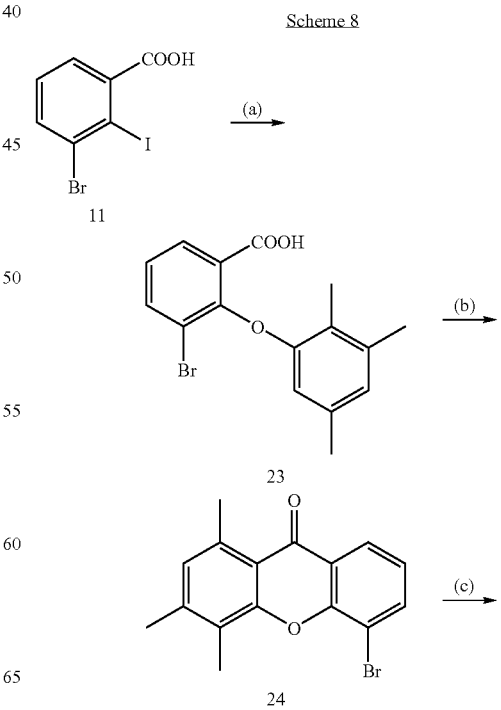

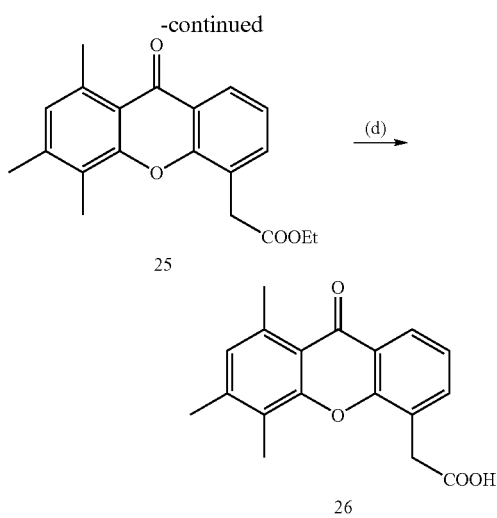

(a) 2,3,5-trimethylphenol/Cu/TDA-1
(b) H$_2$SO$_4$
(c) CH$_2$(COOEt)$_2$/Pd
(d) NaOH Preparation of 3-bromo-2-(2,3,5-trimethylphenoxy benzoic acid (23)

Following the method in Example 1, a crude product of compound 23 was prepared from starting materials of 3-bromo-2-iodo benzoic acid and 2,3,5-trimethylphenol, and the yield was 70%.

Preparation of 4-bromo-5,6,8-trimethylxanthone (24)

Following the method in Example 1, the crude product 23 was treated with sulfuric acid to yield a light yellow solid, and the yield was 85%: mp (EtOAc/MeOH) 230-231° C.; $^1$H-NMR [(CD$_3$)$_2$SO] δ 8.12 (s, 1H), 8.06 (dd, J=7.9, 1.7 Hz, 1H), 7.79 (dd, J=7.3, 1.6 Hz, 1H), 7.42 (dd, J=7.6, 7.6 Hz, 1H), 3.98 (s, 3H), 2.49 (s, 3H), 2.48 (s, 3H); $^{13}$C-NMR δ 171.6, 153.6, 152.1, 143.3, 136.9, 128.0, 125.6, 125.3, 124.5, 123.9, 120.2, 120.0, 119.7, 20.3, 19.4, 19.0.

Preparation of 5,6,8-trimethylxanthone-4-ethyl acetate (25)

Refined 4-bromo-5,6,8-trimethylxanthone (24) (2.3 g, 7.25 mmol), 1,3-bi-(2,6-diisopropylphenyl) imidazole chloride (Ipr. HCl, 60 mg, 0.15 mmol, 2% by mole), Pd(OAc)$_2$ (35 mg, 2% by mole), Cs$_2$CO$_3$ (4.7 g, 14.5 mmol), diethyl malonate (1.16 g, 7.25 mmol), and 20 mL of dioxane were mixed. The mixture was heated at 80° C. for 24 h, then cooled down to room temperature, diluted with 100 mL of ethyl acetate, and filtered to yield a black precipitate. The filtrate was condensed and recrystallized from EtOAc/MeOH to yield a light yellow solid (25) (1.8 g, 85%): mp (EtOAc/MeOH) 209-211° C.; $^1$H-NMR [(CD$_3$)$_2$SO] δ 8.12 (s, 1H), 8.06 (dd, J=7.9, 1.7 Hz, 1H), 7.79 (dd, J=7.3, 1.6 Hz, 1H), 7.42 (dd, J=7.6, 7.6 Hz, 1H), 3.98 (s, 2H), 2.49 (s, 3H), 2.48 (s, 3H), 2.44 (s, 3H), 2.21 (m, 3H); $^{13}$C-NMR δ 175.0, 171.6, 153.6, 152.1, 143.3, 136.9, 128.0, 125.6, 125.3, 124.5, 123.9, 120.2, 120.0, 119.7, 60.5, 53.3, 20.3, 21.0, 12.4.

Preparation of 5,6,8-trimethylxanthone-4-sodium acetate

Following the method in Example 1, the title compound was prepared.

EXAMPLE 5

Cytotoxic activity of the compounds represented by formula (I) was measured by the following method.

Clone No. 38 tumor was obtained from Mason Research Inc. and injected into experimental mice. The compounds represented by the formula (I) was dissolved in brine and administered by peritoneal injection, and the dosage thereof was gradually increased to a maximum tolerated dose by 1.5 times the interval. Each dosage level was measured independently at least two times (commonly, three times). For each measurement, each group had five mice. The anti-tumor effect of the compounds was measured through short-term tissue assay.

The results were listed in Table 2.

TABLE 2

Cytotoxic activity of the compounds represented by formula (I)

| NO | R | OD | Activity |
|---|---|---|---|
| 1 | H | 30 | ++ |
| 2 | 2-CH$_3$ | 25 | ++ |
| 3 | 7-CH$_3$ | 30 | ++ |
| 4 | 8-CH$_3$ | 30 | ++ |

OD refers to the minimum dose (mg/Kg) of brine injection administered by peritoneal injection and causing activity; ++ refers to >90% of cross section is necrotic.

The results showed the measured compounds had anticancer activity, and were even more effective than DMXAA.

Additionally, the results showed the compounds as anticancer drugs were effective, particularly against solid tumors, and had immune-stimulating activity.

Therefore, the invention further provides a pharmaceutical composition comprising the compounds represented by formula (I) and a pharmaceutically acceptable salt thereof for treatment of tumors.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A method of preparing 5,6-dimethylxanthenone-4-acetic acid, comprising the steps of:

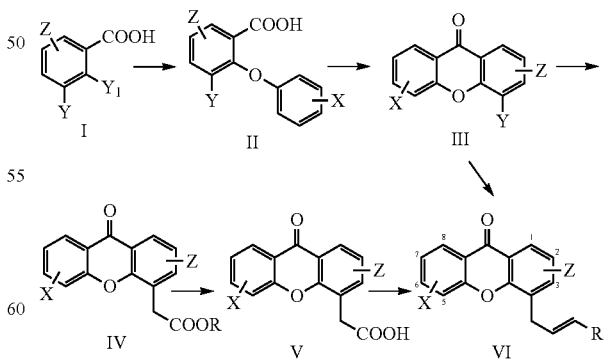

wherein
X represents H, or totally 0 to 4 substitutes at 5-8 position selected from R, OR, halogen, NO$_2$, NR$_2$, SR, SO$_2$R, CF$_3$, CN, CO$_2$R, CONHR, or COR, wherein R represents a $C_{1-6}$ aliphatic group, $C_{3-6}$ saturated ring substitute, OH, methoxy, $NH_2$, or $N(methyl)_2$, and $R_2$ represents a lower alkyl, or a lower alkyl comprising OH, $NH_2$, or $OCH_3$;

Y represents a halogen selected from Cl, Br, or I;

$Y_1$ represents a halogen selected from Cl, Br, or I; and

Z represents H, or totally 0 to 3 substitutes at 1-3 position selected from R, OR, halogen, $NO_2$, $NR_2$, SR, $SO_2R$, $CF_3$, CN, $CO_2R$, CONHR, or COR, wherein R represents a $C_{1-6}$ aliphatic group, $C_{3-6}$ saturated ring substitute, OH, methoxy, $NH_2$, or $N(methyl)_2$, and $R_2$ represents a lower alkyl, or a lower alkyl comprising OH, $NH_2$, or $OCH_3$.

2. The method of claim 1, wherein X represents 5,6-dimethyl, 5,6-dimethoxy, 5-Cl, 6-methyl, 5-Cl, or 6-methoxy; Y represents Br; $Y_1$ represents I; and Z represents H, 2-methyl, 2-methoxy, or 2-Cl.

3. The method of claim 2, wherein X represents 5,6-dimethyl; Y represents Br; $Y_1$ represents I; and Z represents H.

4. The method of claim 3, wherein during the conversion reaction of the compound (I) into the compound (II), 2,3-dimethylphenol or 2,3,5-trimethylphenol is reacted with compound (I).

5. The method of claim 3, wherein compound (I) is 3-bromo-2-iodo benzoic acid, or 3-bromo-2-iodo-5-methylbenzoic acid.

6. The method of claim 1, wherein during the conversion reaction of the compound (I) into the compound (II), a catalyst is CuCl and tris(2-(2-methoxyethoxy)ethyl)amine.

7. The method of claim 1, wherein during the conversion reaction of the compound (II) into the compound (III), a dehydration-cyclization agent is sulfuric acid, methanesulfonic acid, polyphosphoric acid, or polyphosphate.

8. The method of claim 1, wherein during the conversion reaction of the compound (III) into the compound (IV), a catalyst is a palladium-containing agent and complex, and said complex is 1,3-bi-(2,6-diisopropylphenyl) imidazole chloride.

* * * * *